United States Patent
Nagamizu et al.

(10) Patent No.: US 10,197,785 B2
(45) Date of Patent: Feb. 5, 2019

(54) INSPECTION DEVICE FOR IMAGE PICKUP APPARATUS

(71) Applicant: OLYMPUS CORPORATION, Tokyo (JP)

(72) Inventors: Hiroyuki Nagamizu, Sagamihara (JP); Kenji Omachi, Hachioji (JP); Kazuyoshi Jingu, Inagi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/674,095

(22) Filed: Aug. 10, 2017

(65) Prior Publication Data

US 2018/0024349 A1   Jan. 25, 2018

Related U.S. Application Data

(63) Continuation of application No. PCT/JP2016/075221, filed on Aug. 29, 2016.

(30) Foreign Application Priority Data

Nov. 6, 2015 (JP) ................................. 2015-218680

(51) Int. Cl.
*A61B 1/00* (2006.01)
*G02B 23/24* (2006.01)
(Continued)

(52) U.S. Cl.
CPC ...... *G02B 23/2484* (2013.01); *A61B 1/00057* (2013.01); *A61B 1/00096* (2013.01);
(Continued)

(58) Field of Classification Search
CPC .... G02B 23/2484; A61B 1/05; A61B 1/00057
(Continued)

(56) References Cited

U.S. PATENT DOCUMENTS

2008/0123087 A1   5/2008   Chen

FOREIGN PATENT DOCUMENTS

CN   101191995 A   6/2008
JP   S49-085929 A   7/1974
(Continued)

OTHER PUBLICATIONS

International Search Report dated Oct. 11, 2016 issued in PCT/JP2016/075221.

*Primary Examiner* — Jeffery A Williams
(74) *Attorney, Agent, or Firm* — Scully, Scott, Murphy & Presser, P.C.

(57) ABSTRACT

An inspection device for image pickup apparatus includes: an image pickup apparatus including an image pickup device inside a first lens barrel; an angle-of-view conversion optical member made of a translucent resin member and including a first surface and a second surface that is an opposite surface of the first surface, the first surface being configured to closely contact a surface of a distal end lens, the surface of the distal end lens being exposed outside of the first lens barrel; a test chart including a chart surface provided so as to closely contact the second surface, and an image of the chart surface being picked up by the image pickup apparatus through the angle-of-view conversion optical member, and an illumination instrument that illuminates the chart surface.

4 Claims, 9 Drawing Sheets

(51) Int. Cl.
*A61B 1/05* (2006.01)
*H04N 5/225* (2006.01)
*H04N 17/00* (2006.01)
*H04N 9/07* (2006.01)

(52) U.S. Cl.
CPC ............. *A61B 1/05* (2013.01); *G02B 23/24* (2013.01); *G02B 23/243* (2013.01); *G02B 23/2461* (2013.01); *H04N 5/2254* (2013.01); *H04N 5/2256* (2013.01); *H04N 17/002* (2013.01); *H04N 9/07* (2013.01); *H04N 2005/2255* (2013.01)

(58) Field of Classification Search
USPC .......................................................... 348/68
See application file for complete search history.

(56) References Cited

FOREIGN PATENT DOCUMENTS

| | | | |
|---|---|---|---|
| JP | S63-084383 | A | 4/1988 |
| JP | H09-000056 | U | 1/1997 |
| JP | 2004-121298 | A | 4/2004 |
| JP | 2007-244679 | A | 9/2007 |
| JP | 2011-064744 | A | 3/2011 |
| JP | 2013-195349 | A | 9/2013 |
| JP | 2013195349 | A * | 9/2013 |
| JP | 5379545 | B2 | 10/2013 |

\* cited by examiner

INSPECTION DEVICE FOR IMAGE PICKUP APPARATUS

CROSS REFERENCE TO RELATED APPLICATION

This application is a continuation application of PCT/JP2016/075221 filed on Aug. 29, 2016 and claims benefit of Japanese Application No. 2015-218680 filed in Japan on Nov. 6, 2015, the entire contents of which are incorporated herein by this reference.

BACKGROUND OF THE INVENTION

1. Field of the Invention

The present invention relates to an inspection device for image pickup apparatus that performs image inspection of an image pickup apparatus operated in a liquid and an endoscope incorporating the image pickup apparatus.

2. Description of the Related Art

In recent years, endoscopes have been used in medical fields and industrial fields.

Endoscopes include, what is called an electronic endoscope (hereinafter, just referred to as endoscope) incorporating, in a distal end portion of an insertion portion, an image pickup apparatus provided with an image sensor such as CCD, CMOS, or the like.

Such an endoscope obtains an endoscopic image by image-forming an optical image of an object illuminated with illumination light on a light-receiving surface of the CCD, for example, provided in the image pickup apparatus.

Endoscopes include an endoscope for in-gas observation (hereinafter, shortly referred to as in-gas endoscope) and an endoscope for in-liquid observation (hereinafter, shortly referred to as in-liquid endoscope).

The in-gas endoscope acquires an endoscopic image of an object in a gas, mainly in the air. The in-gas endoscope is, for example, an endoscope for stomach, duodenum, bronchus, large intestine, or the like. On the other hand, the in-liquid endoscope is soaked mainly in water, to acquire an endoscopic image of an object in a liquid. The in-liquid endoscope is, for example, a cystoscope, an industrial endoscope, or the like.

Japanese Patent Application Laid-Open Publication No. 2007-244679 shows the endoscope apparatus that is capable of observing an inside of the bladder, and Japanese Patent No. 5379545 shows the endoscope that is soaked in the water in the nuclear reactor, to be used for inspection of the pipe located in the vicinity of the reactor core.

The refractive index of the water, for example, which is a liquid is different from the refractive index of the air, for example, which is gas.

Therefore, a diameter size of an image circle formed on a rectangular light-receiving area La, for example, of an image pickup device changes in the in-liquid observation performed by the in-liquid endoscope and in the in-gas observation performed by the in-liquid endoscope, as shown in FIG. 1.

Specifically, a radius R1 of a first image circle in the in-gas observation, which is shown by the dashed line is smaller than a radius R2 of a second image circle in the in-liquid observation, which is shown by the two-dot chain line.

As a result, at the time of the in-liquid observation, light is applied on the entire surface of the light-receiving area La. On the other hand, at the time of the in-gas observation, an area shaded from the light (hatching portion indicated by the reference sign Sa in the drawings) is created in the peripheral portion of the light-receiving area La. The area Sa shaded from the light in the light-receiving area La is a completely dark part in an endoscopic image displayed on the display screen of the observation apparatus, what is called a vignetting portion.

Therefore, inspection of the image pickup apparatus provided with an image pickup optical system, an objective optical system, and the like that are used in an in-liquid endoscope is performed in the gas, a vignetting portion is generated in the inspection image, and it is impossible to confirm whether a fine dirt such as dust of wire bonding is present or whether delamination occurs on the bonding surface of the optical adhesive in the vignetting portion.

Note that when the above-described defect is present in the vignetting portion in the light-receiving area of the image pickup device incorporated in the in-liquid endoscope, optical defects such as reflection of dust on the endoscopic image at the time of in-liquid observation or a smudgy endoscopic image occur, which causes ill effects on the endoscopic observation.

As an inspection method for solving these optical defects, it is considered that the objective optical system of the image pickup apparatus used in the in-liquid endoscope is soaked in a liquid.

SUMMARY OF THE INVENTION

An inspection device for image pickup apparatus according to one aspect of the present invention is an inspection device for image pickup apparatus and includes: an angle-of-view conversion optical member made of a translucent member having a predetermined refractive index, the angle-of-view conversion optical member including a first surface and a second surface that is an opposite surface of the first surface, the first surface being configured to closely contact a surface of a distal end optical member constituting an optical system of the image pickup apparatus, the surface of the distal end optical member being exposed outside of an exterior body of the image pickup apparatus, wherein a thickness from the second surface to the first surface is set to a predetermined dimension; a test chart including a chart surface provided so as to closely contact the second surface of the angle-of-view conversion optical member, an image of the chart surface being picked up by the image pickup apparatus through the angle-of-view conversion optical member; and an illumination portion that illuminates the chart surface of the test chart, wherein the test chart is a reflection chart, and the chart surface of the reflection chart is irradiated with illumination light that is emitted from the illumination portion and enters the angle-of-view conversion optical member from a side surface located between the first surface and the second surface of the angle-of-view conversion optical member.

An inspection device for image pickup apparatus according to one aspect of the present invention is an inspection device for image pickup apparatus and includes: an angle-of-view conversion optical member made of a translucent member having a predetermined refractive index, the angle-of-view conversion optical member including a first surface and a second surface that is an opposite surface of the first surface, the first surface being configured to closely contact a surface of a distal end optical member constituting an optical system of the image pickup apparatus, the surface of the distal end optical member being exposed outside of an exterior body of the image pickup apparatus, wherein a thickness from the second surface to the first surface is set to a predetermined dimension; a test chart including a chart surface provided so as to closely contact the second surface of the angle-of-view conversion optical member, an image of the chart surface being picked up by the image pickup apparatus through the angle-of-view conversion optical member; and an illumination portion that illuminates the chart surface of the test chart, wherein the test chart is a transmission chart, and the chart surface of the transmission chart is irradiated with illumination light that is emitted from the illumination portion and enters the distal end optical member from a surface opposite to the chart surface of the test chart.

DETAILED DESCRIPTION OF THE PREFERRED EMBODIMENTS

Figure 1:
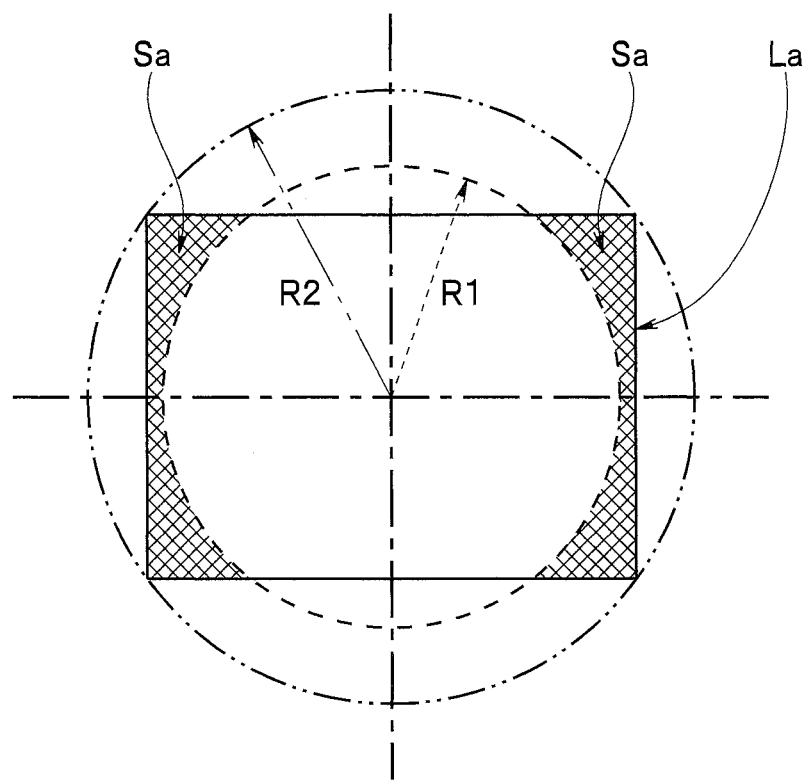
FIG. 1 illustrates a relation between an image circle at a time of in-liquid observation and an image circle at a time of in-gas observation by an image pickup apparatus of an in-liquid endoscope, and a light-receiving area of the image pickup apparatus.

Hereinafter, embodiments of the present invention are described with reference to drawings.

Note that, in the drawings used in the description below, there is a case where a different scale size is used for each of the constituent elements in order to allow each of the constituent elements to be illustrated in a recognizable size in the drawings. That is, the present invention is not limited to the number, shapes, ratio of the sizes of the constituent elements, and a relative positional relationship among the respective constituent elements shown in these drawings.

Figure 2:
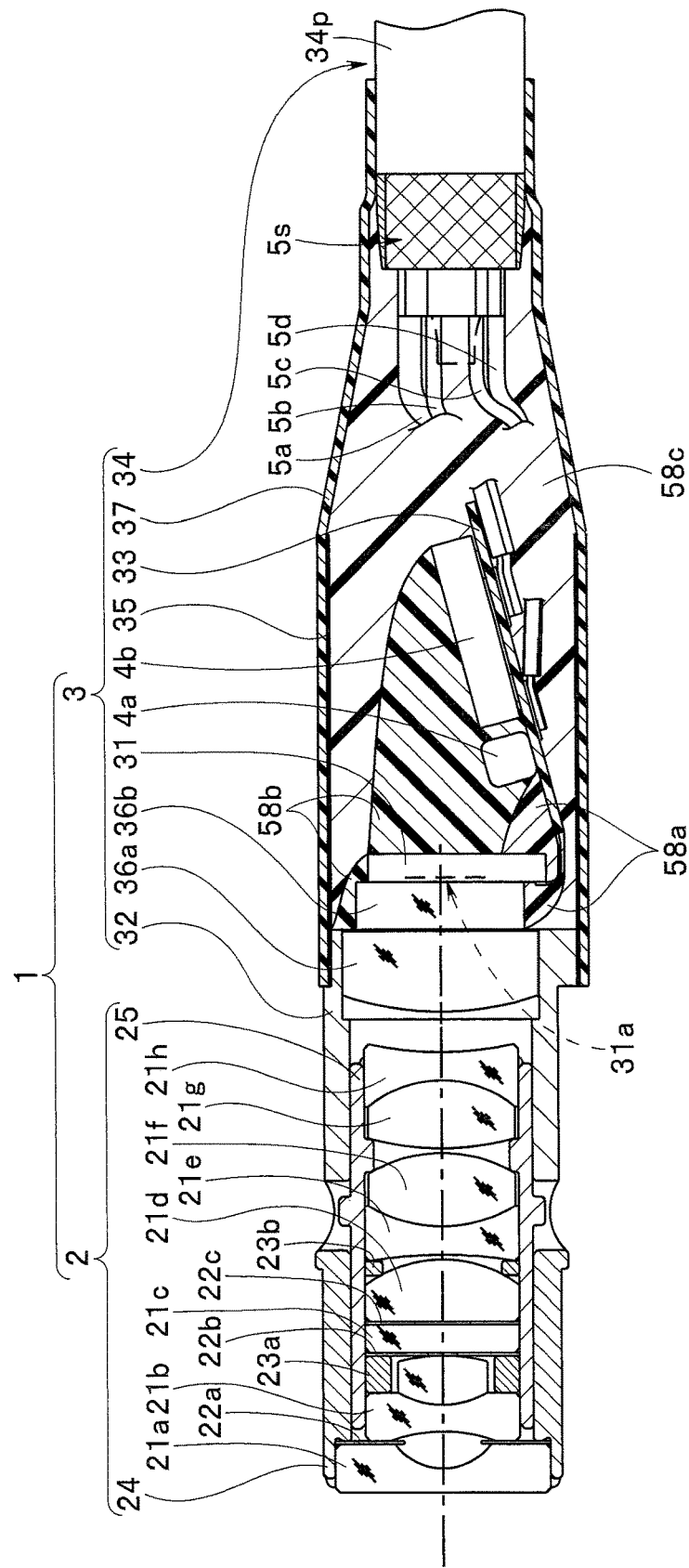
FIG. 2 illustrates the image pickup apparatus used in the in-liquid endoscope.

The reference numeral 1 in FIG. 2 indicates an image pickup apparatus which is used in an endoscope for in-liquid observation for acquiring an endoscopic image of an object in the bladder.

The image pickup apparatus 1 includes an optical unit 2 as an objective optical system, and a device unit 3 as an image pickup optical system. The optical unit 2 includes, for example, optical members such as a plurality of optical lenses 21, a plurality of diaphragms 22, spacing rings 23 and the like, and lens barrels 24, 25 made of stainless steel, for example, to which the optical lenses 21, the diaphragms 22, and the spacing rings 23 are fixed.

In the present embodiment, the first lens barrel 24 is an exterior body of the image pickup apparatus 1. A distal end lens 21a which is a distal end optical member to be described later is integrally fixed to the first lens barrel 24 by adhesion or bonding. The surface of the distal end lens 21a is exposed to the outside of the first lens barrel 24.

The distal end portion of the second lens barrel 25 is disposed on the proximal end inner surface of the first lens barrel 24 and integrally fixed by adhesion or bonding. In the second lens barrel 25, the optical lenses $21b, \ldots, 21k$, the diaphragms 22a, 22b, 22c, the spacing rings 23a, 23b, and the like are disposed.

The device unit 3 includes an image pickup device 31, a device barrel 32, a circuit substrate 33, a signal cable 34, an image pickup apparatus exterior barrel (hereinafter, referred to as exterior barrel) 35. The device barrel 32 is also an exterior body that constitutes the exterior of the image pickup apparatus 1.

The image pickup device 31 is CCD, CMOS, or the like. Two cover lenses 36a, 36b, which are optical members, for example, are adhered and fixed to a light-receiving surface 31a side of the image pickup device 31, which is shown by the dashed line, with transparent adhesive. The second cover lens 36b is adhered and fixed to the light-receiving surface of the image pickup device 31.

In the present embodiment, the first cover lens 36a, which is disposed closer to the optical unit 2 with respect to the second cover lens 36b, is integrally fixed to the inner surface of the proximal end portion of the device barrel 32 made of stainless steel by adhesion or bonding.

The proximal end portion of the second lens barrel 25 is disposed on the inner surface of the distal end portion of the device barrel 32, and after positional adjustment such as focus adjustment is completed, the second lens barrel 25 and the device barrel 32 are integrally bonded to each other by solder 51, for example.

As a result, the optical system of the image pickup apparatus 1, which includes the optical members such as a plurality of optical lenses 21, a plurality of diaphragms 22, the spacing rings 23, etc., and cover lenses 36a, 36b on the light-receiving surface 31a side of the image pickup device 31, is configured. With the optical system of the image pickup apparatus 1, the optical image of an object, which enters from the distal end lens 21a, passes through the optical system, to be formed on the light-receiving surface 31a of the image pickup device 31.

The circuit substrate 33 is a flexible printed circuit board having flexibility, for example. Various kinds of electronic parts 4a, 4b, and the like are mounted on the circuit substrate 33. The distal end side of the circuit substrate 33 on which the electronic parts 4a, 4b are mounted is electrically connected to the image pickup device 31.

A plurality of signal lines 5a, 5b, 5c, 5d, . . . are inserted in the signal cable 34. The distal end portions of the plurality of signal lines 5a, 5b, 5c, 5d, . . . are connected to an electric connection portion, not shown, provided on the circuit substrate 33. The plurality of signal lines 5a, 5b, 5c, 5d, . . . are coaxial cables, and single wires, for example. The reference numeral 5s indicates an external conductor portion, which is formed by integrating the external conductors of the coaxial cables.

An exterior barrel 35 configures the exterior of the device unit 3. The exterior barrel 35 is formed in a predetermined shape by rolling up or bending one rectangular thin plate made of stainless steel, for example. The exterior barrel 35 covers and wraps the image pickup device 31, the circuit substrate 33 on which the electronic parts 4a, 4b, etc., are mounted, and a part of the signal lines 5a, 5b, 5c, 5d . . . which are connected to the circuit substrate 33.

A thin-walled heat-shrinkable tube 37 is disposed on the outer surface of the exterior barrel 35. The proximal end portion of the heat-shrinkable tube 37 is fixed to the outer surface of the distal end portion of a protection member 34p that configures the exterior of a signal cable 34.

Note that insulating sealing resins 58a, 58b, and 58c are provided in the exterior barrel 35 and the heat-shrinkable tube 37. Specifically, the first sealing resin 58a is provided so as to cover the periphery of an electric connection portion between the circuit substrate 33 and the image pickup device 31. The second sealing resin 58b is provided so as to cover the peripheries of the electronic parts 4a, 4b mounted on the circuit substrate 33, and the peripheries of the cover lens 36b and image pickup device 31. The third sealing resin 58c is filled around the connection portion between the signal lines 5a, 5b, 5c, . . . , and the circuit substrate 33, and the space configured mainly by the exterior barrel 35, the device barrel 32, and the second sealing resin 58b.

Figure 3:
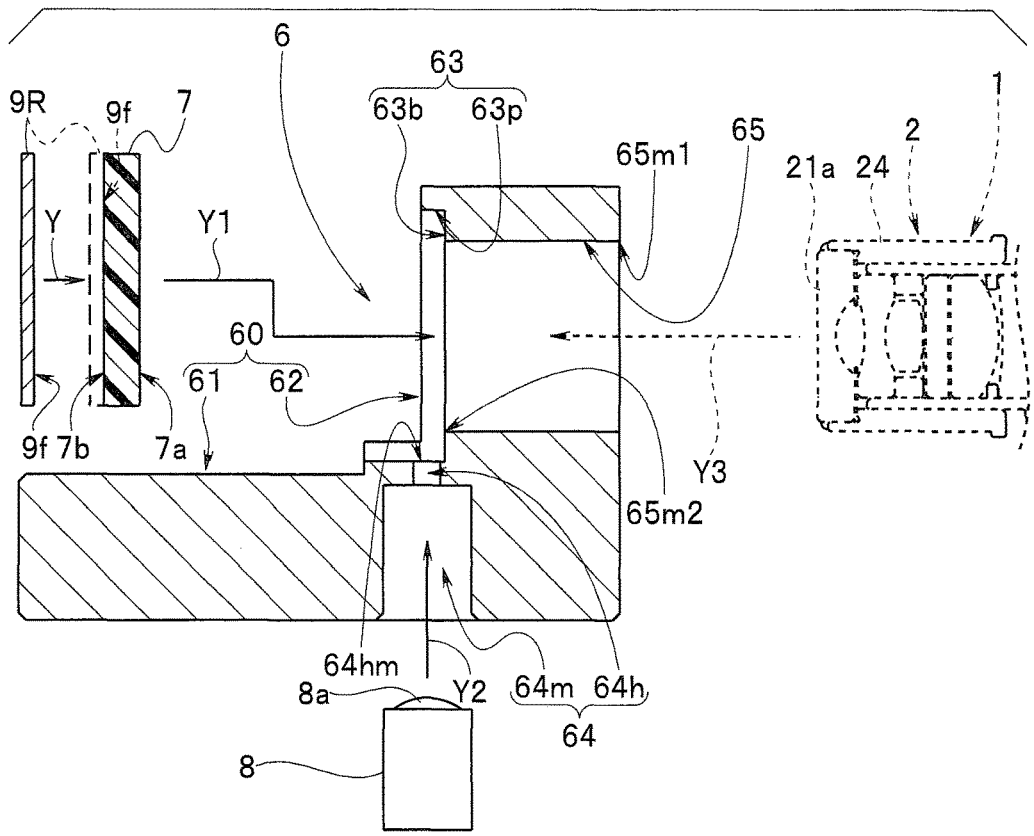
FIG. 3 illustrates a configuration of an image pickup apparatus inspection device and a relation between the image pickup apparatus inspection device and the image pickup apparatus.
Figure 4:
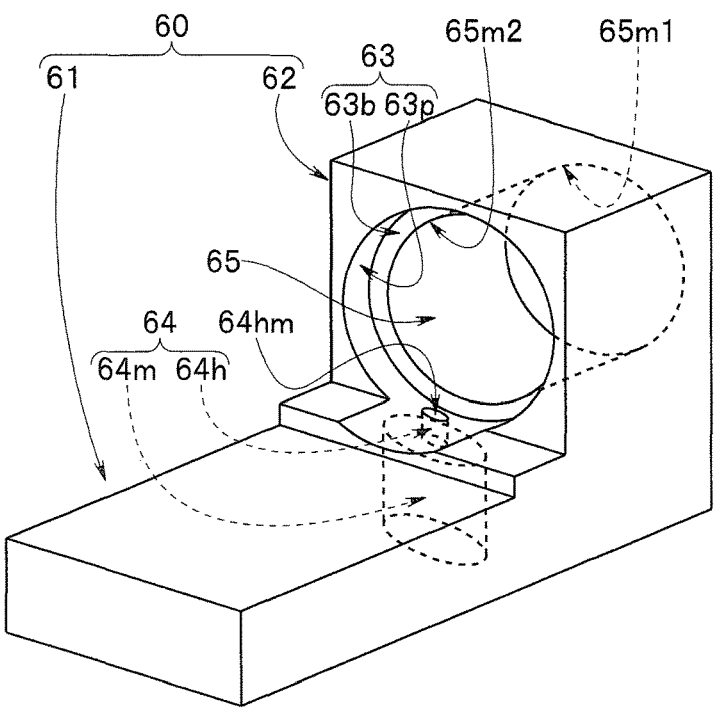
FIG. 4 illustrates a case for inspection.

With reference to FIGS. 3 and 4, description will be made on an image pickup apparatus inspection device 6 which is a jig for inspecting observation performance of the image pickup apparatus 1 configured as described above in a gas.

As shown in FIGS. 3, 4, the image pickup apparatus inspection device 6 includes a case for inspection 60, an angle-of-view conversion optical member 7, an illumination instrument 8 as an illumination portion, and a test chart 9 that are disposed in the case 60. The illumination instrument 8 is an LED lighting, for example. The reference numeral 8a indicates an illumination lens.

Figure 5A:
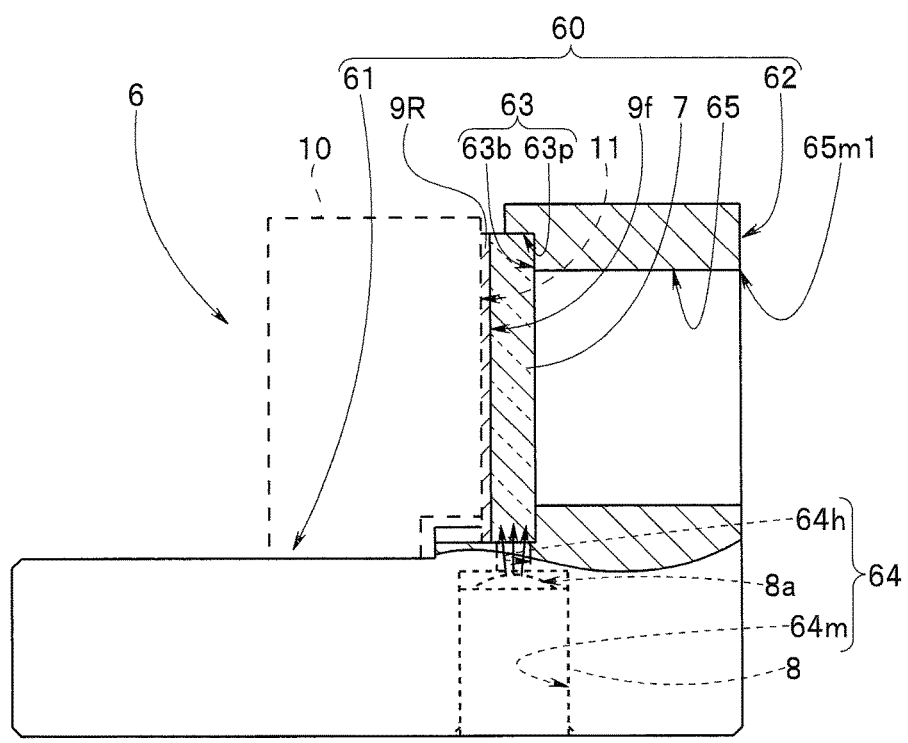
FIG. 5A illustrates a configuration of the image pickup apparatus inspection device provided with a reflection chart.
Figure 5B:
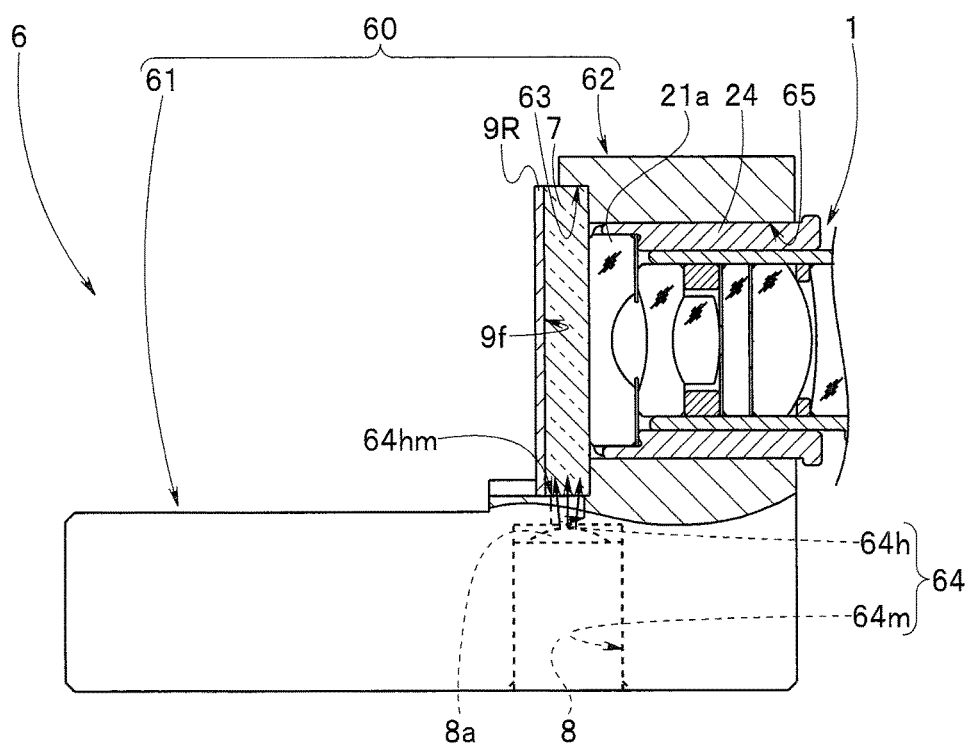
FIG. 5B illustrates an inspection state where the image pickup apparatus is disposed in the image pickup apparatus inspection device in FIG. 5A.

Note that the test chart 9 includes a reflection chart 9R of the present embodiment, and a transmission chart 9T to be described later. FIGS. 3, 5A, and 5B show the test chart 9 as the reflection chart 9R.

The angle-of-view conversion optical member 7 is formed in a disk shape, for example, and includes a first surface 7a and a second surface 7b which is an opposite surface of the first surface 7a. The angle-of-view conversion optical member 7 is formed by a translucent member having a predetermined resiliency. Specifically, the angle-of-view conversion optical member 7 is made of fluorine resin, the refractive index of which is same as that of water, or silicone rubber, acrylic rubber, or elastomer, the refractive index of which is larger than that of water.

The outer diameter of the angle-of-view conversion optical member 7 is set to be larger than the outer diameter of the distal end lens 21a of the image pickup apparatus 1. The thickness from the first surface 7a to the second surface 7b of the angle-of-view conversion optical member 7 is set to a distance in which the image pickup apparatus 1 is capable of performing image pickup operation in a liquid.

The first surface 7a of the angle-of-view conversion optical member 7 is a plane with which the surface of the distal end lens 21a comes into close contact, and the angle-of-view conversion optical member 7 elastically deforms, to thereby allow the surface of the distal end lens 21a to be disposed so as to closely contact the first surface 7a in a state where no air layer exists.

The second surface 7b of the angle-of-view conversion optical member 7 is a plane on which the reflection chart 9R is disposed. The reflection chart 9R includes on one surface thereof a chart surface 9f, and on the chart surface 9f, a pattern including a color chart of a single color such as red, green, blue, white, etc., a color chart colored with a plurality of colors, or a test chart for checking a resolution is drawn, for example.

The reflection chart 9R is provided integrally with the angle-of-view conversion optical member 7. Specifically, the chart surface 9f of the reflection chart 9R is moved as shown by the arrow Y to be disposed on the second surface 7b of the angle-of-view conversion optical member 7, and tightly fixed to the second surface 7b by a transparent adhesive or the like in the state where no air layer exists between the second surface 7b and the chart surface 9f.

The case for inspection 60 is an inspection device main body and includes a support portion 61 and an inspection convex portion 62. The case for inspection 60 is provided with an optical member housing hole 63, an illumination instrument housing hole 64, and an exterior body insertion hole 65.

The support portion 61 is a pedestal of the case for inspection 60. The case for inspection 60 can be fastened and fixed to a work bench with a clamp, not shown.

The inspection convex portion 62 is a convex portion protruded from the upper plane in the drawing, which is one surface of the support portion 61. In the present embodiment, the optical member housing hole 63 and the exterior body insertion hole 65 are formed at the inspection convex portion 62, and the illumination instrument housing hole 64 is formed at the support portion 61.

Note that the illumination instrument housing hole 64 is formed at the support portion 61. However, the illumination instrument housing hole 64 may be provided at the inspection convex portion 62 by appropriately deforming the shape of the inspection convex portion 62.

The optical member housing hole 63 is a first attaching portion, and the inner diameter and the depth thereof is set in view of the outer diameter and the thickness of the angle-of-view conversion optical member 7. In the optical member housing hole 63, the angle-of-view conversion optical member 7 to which the reflection chart 9R is integrally provided is disposed as shown by the arrow Y1 in FIG. 3, and adhered and fixed by adhesive, for example, as shown in FIG. 5A.

The illumination instrument housing hole 64 is a second attaching portion, and includes a housing hole main body 64m and a light-guiding hole 64h. An emission opening 64hm of the light-guiding hole 64h is formed on an inner circumferential surface 63p of the optical member housing hole 63. As shown by the arrow Y2 in FIG. 3, the illumination instrument 8 is inserted in the housing hole main body 64m, to be housed and disposed, and installed in a predetermined state by a lid member, not shown, or adhesive or the like, as shown in FIG. 5A.

As a result, the image pickup apparatus inspection device 6, which includes the angle-of-view conversion optical member 7 to which the reflection chart 9R is integrally provided and the illumination instrument 8, is configured in the case for inspection 60.

With this image pickup apparatus inspection device 6, the illumination light of the illumination instrument 8 passes through the light-guiding hole 64h, to be emitted from the emission opening 64hm, and enters the angle-of-view conversion optical member 7 from the side surface of the angle-of-view conversion optical member 7 disposed on the inner circumferential surface 63p of the optical member housing hole 63.

As a result, the chart surface 9f is irradiated with the illumination light of the illumination instrument 8.

The exterior body insertion hole 65 is a third attaching portion, and is a straight-shaped through hole, for example, corresponding to the outer shape of the first lens barrel 24. As shown by the arrow Y3 indicated by the dashed line in FIG. 3, the first lens barrel 24 of the image pickup apparatus 1 is inserted into the exterior body insertion hole 65. The exterior body insertion hole 65 includes an insertion port 65m1 into which the first lens barrel 24 is inserted and a lead-out port 65m2 from which the first lens barrel 24 can be led out.

The lead-out port 65m2 is an opening formed on a bottom surface 63b of the optical member housing hole 63. The diameter of the lead-out port 65m2 is smaller than the diameter of the optical member housing hole 63. Therefore, the lead-out port 65m2 is blocked by the angle-of-view conversion optical member 7 fixed in the optical member housing hole 63.

Description will be made on the working of the image pickup apparatus inspection device 6 configured as described above.

The worker disposes the proximal end portion of the second lens barrel 25 on the inner surface of the distal end portion of the device barrel 32 to perform positional adjustment such as focus adjustment, and thereafter integrally bonds the second lens barrel 25 and the device barrel 32 to form the image pickup apparatus 1. After that, the worker performs, in the gas, the inspection of whether dust is present on the entire surface of the light-receiving area of the image pickup apparatus, or whether delamination occurs on the bonding surface of the optical adhesive.

At this time, the worker prepares an inspection apparatus including the image pickup apparatus inspection device 6 shown in FIG. 5A and a display screen, to turn on the illumination instrument 8. After that, the worker disposes the first lens barrel 24 of the image pickup apparatus 1 in the exterior body insertion hole 65 of the image pickup apparatus inspection device 6, as shown in FIG. 5B.

Specifically, the worker grasps the device barrel 32, for example, to insert the first lens barrel 24 from the insertion port 65m1. Then, the worker causes the distal end lens 21a positioned at the distal end of the first lens barrel 24 to advance toward the chart surface 9f. Then, the surface of the distal end lens 21a abuts the first surface 7a of the angle-of-view conversion optical member 7.

The worker causes the first lens barrel 24 to advance by inches, to bring the surface of the distal end lens 21a into close contact with the first surface 7a of the angle-of-view conversion optical member 7.

As a result, the pattern on the chart surface 9f of the reflection chart 9R illuminated with the illumination light incident on the optical member 7 passes through the angle-of-view conversion optical member 7, to be image-formed on the light-receiving surface 31a of the image pickup device 31 of the image pickup apparatus 1.

The refractive index of the angle-of-view conversion optical member 7 is set to be equal to or larger than the refractive index of water, thereby allowing an endoscopic image corresponding to the endoscopic image in the in-liquid observation, which is formed on the light-receiving surface 31a of the image pickup device 31 of the image pickup apparatus 1, to be displayed on the display screen of the inspection apparatus.

In other words, the endoscopic image whose size is equal to or larger than the diameter of the second image circle R2 as shown in FIG. 1 which does not include in the peripheral portion thereof an area shaded from the light is formed on the light-receiving surface 31a of the image pickup device 31.

As a result, the endoscopic image in which no vignetting portion exists is displayed on the display screen of the inspection apparatus, which enables the inspection of defect such as the inspection of whether fine dust is present or the inspection of whether delamination occurs on the bonding surface of the optical adhesive to be performed.

Thus, inspection is performed by bringing the surface of the distal end lens 21a into close contact with the first surface 7a of the angle-of-view conversion optical member 7 made of the translucent member which has resiliency and the thickness of which is set in view of the refractive index of water. Then, the light which is reflected on the chart surface 9f of the reflection chart 9R closely contacting the second surface 7b of the angle-of-view conversion optical member 7 and which passes through the angle-of-view conversion optical member 7 is image-formed on the light-receiving surface 31a of the image pickup device 31. Therefore, the inspection of the image pickup apparatus 1 can be performed in the gas, with the observation state same as that in the in-liquid observation being obtained.

Note that the reference numeral 10 shown by the dashed line in FIG. 5A indicates a holding block. The holding block 10 is integrally fixed to the support portion 61, for example, with a fastening member such as a bolt, not shown. An abutting surface 11 of the holding block 10 abuts the surface opposite to the chart surface 9f of the reflection chart 9R, to securely hold the angle-of-view conversion optical member 7 to which the reflection chart 9R is integrally provided.

As a result, after the surface of the distal end lens 21a abuts the first surface 7a of the angle-of-view conversion optical member 7, the worker is capable of more easily bringing the surface of the distal end lens 21a into close contact with the first surface 7a of the angle-of-view conversion optical member 7.

In addition, in the above-described embodiment, the test chart 9 of the image pickup apparatus inspection device 6 is the reflection chart 9R. However, the test chart 9 is not limited to the reflection chart 9R, and may be the transmission chart 9T.

Figure 6A:
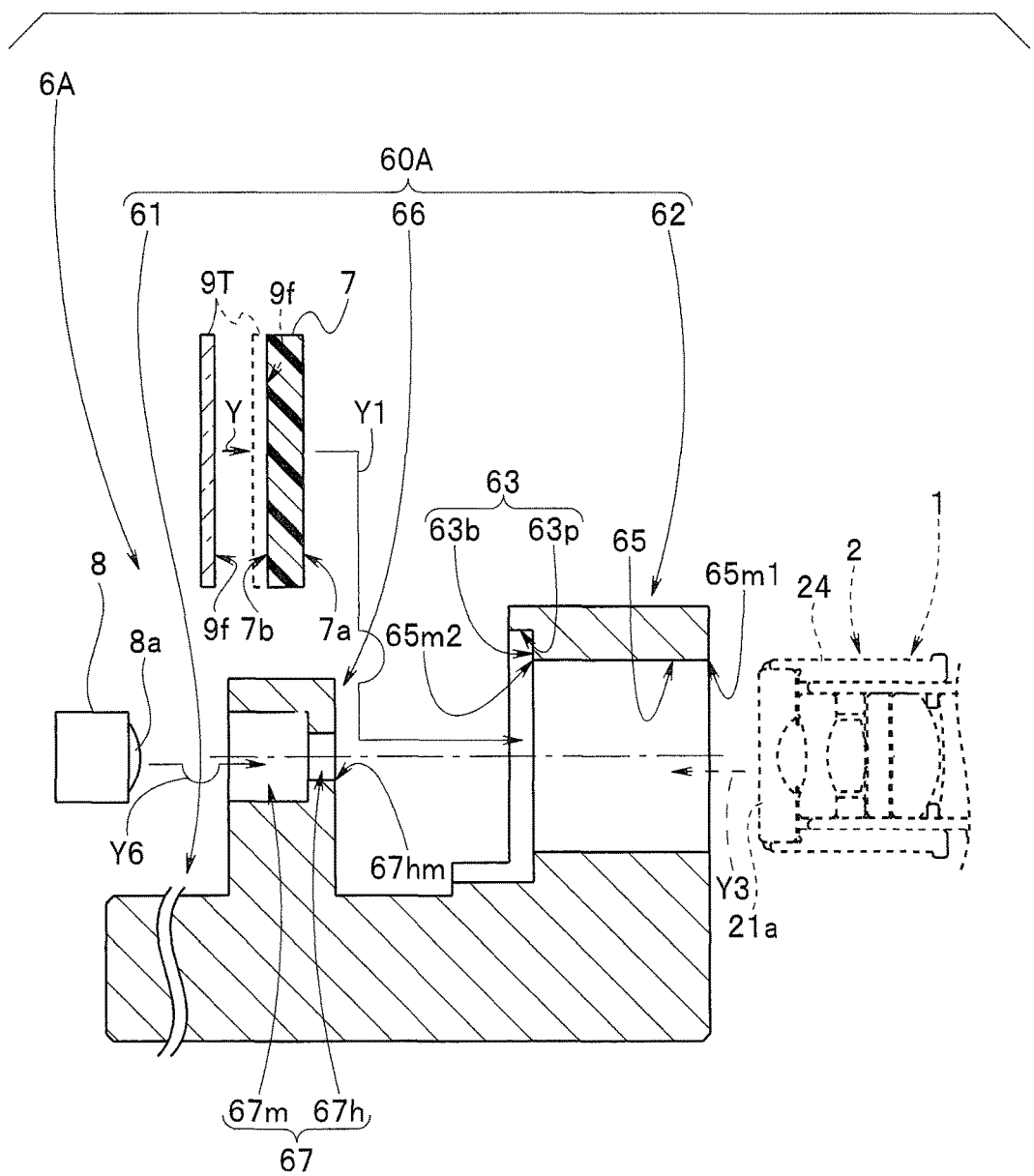
FIG. 6A illustrates a configuration of an image pickup apparatus inspection device provided with a transmission chart, and a relation between the image pickup apparatus inspection device and the image pickup apparatus.
Figure 6B:
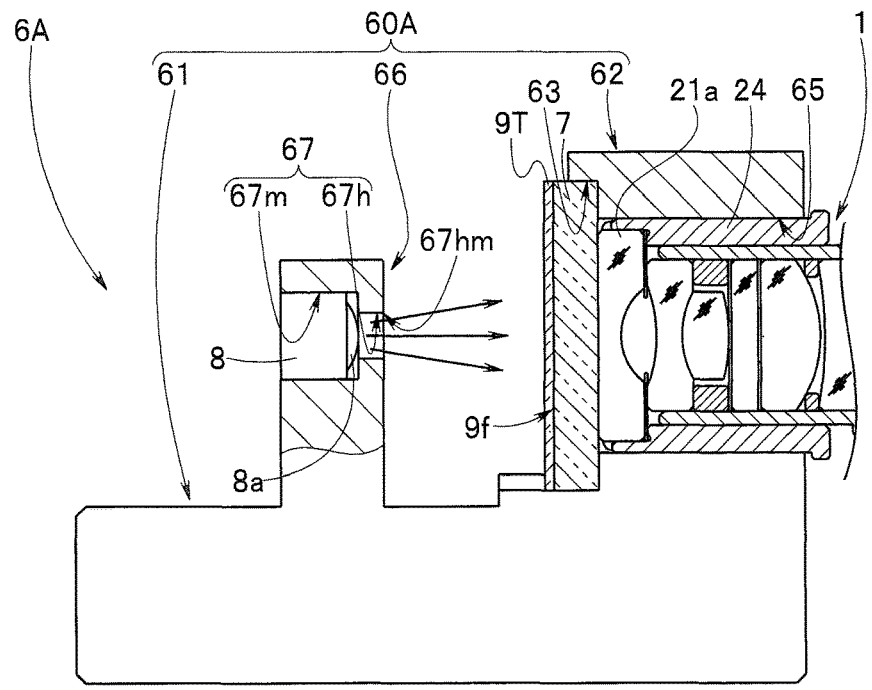
FIG. 6B illustrates an inspection state where the image pickup apparatus is disposed in the image pickup apparatus inspection device in FIG. 6A.

With reference to FIGS. 6A, 6B, description will be made on an exemplary configuration of an image pickup apparatus inspection device 6A provided with the transmission chart 9T.

The image pickup apparatus inspection device 6A includes the transmission chart 9T as the test chart 9. Therefore, in FIGS. 6A, 7, 8B, 10, and 11, the test chart 9 is illustrated as the transmission chart 9T. The transmission chart 9T includes on one face thereof a chart surface 9f, and on the chart surface 9f, a pattern corresponding to the inspection, for example, a color chart of a single color such as red, green, blue, white, etc., a color chart colored with a plurality of colors, or a test chart for checking a resolution is drawn.

The transmission chart 9T is provided integrally with the angle-of-view conversion optical member 7 similarly as in the above-described embodiment. That is, the chart surface 9f of the transmission chart 9T is moved as shown by the arrow Y to be disposed on the second surface 7b of the angle-of-view conversion optical member 7, and tightly fixed by a transparent adhesive or the like in the state where no air layer exists between the second surface 7b and the chart surface 9f. The angle-of-view conversion optical member 7 provided with the transmission chart 9T is disposed in the optical member housing hole 63 similarly as described above, and adhered and fixed to the optical member housing hole 63 by an adhesive, for example, as shown in FIG. 6B.

In the present embodiment, the illumination instrument 8 is housed in an illumination instrument housing hole 67 provided at a convex portion for illumination 66. That is, a case for inspection 60A in the present embodiment is provided with the convex portion for illumination 66.

The convex portion for illumination 66 is a convex portion protruded from the upper plane in the drawing, which is one surface of the support portion 61, and includes a surface opposed to the bottom surface 63b of the optical member housing hole 63. The illumination instrument housing hole 67 is formed at the convex portion for illumination 66.

The illumination instrument housing hole 67 includes a housing hole main body 67m and a light-guiding hole 67h. The illumination instrument 8 is inserted and disposed in the housing hole main body 67m, as shown by the arrow Y6 in FIG. 6A, to be housed and installed in a predetermined state by a lid member, not shown, or by adhesive or the like, as shown in FIG. 6B.

Note that the longitudinal axis of the illumination instrument housing hole 67 and the longitudinal axis of the exterior body insertion hole 65 are set to be coaxial. In addition, the emission opening 67hm is formed on the surface opposed to the bottom surface 63b of the convex portion 66 for illumination.

As a result, the image pickup apparatus inspection device 6A, which includes the angle-of-view conversion optical member 7 to which the transmission chart 9T is integrally provided and the illumination instrument 8, in the case for inspection 60A, is configured.

With the image pickup apparatus inspection device 6A, the illumination light of the illumination instrument 8 passes through the light-guiding hole 67h, to be emitted from the emission opening 67hm toward the rear surface which is opposite surface of the chart surface 9f of the transmission chart 9T provided integrally with the angle-of-view conversion optical member 7 fixed in the optical member housing hole 63. Therefore, the chart surface 9f of the transmission chart 9T is irradiated with the illumination light entered from the rear surface of the transmission chart 9T.

Other configurations are the same as those in the above-described embodiment, and the same elements are attached with the same reference numerals and descriptions thereof will be omitted.

Working of the image pickup apparatus inspection device 6A configured as described above will be described.

The worker disposes the proximal end portion of the second lens barrel 25 on the inner surface of the distal end portion of the device barrel 32 to perform positional adjustment such as focus adjustment, and thereafter integrally bonds the second lens barrel 25 and the device barrel 32 to form the image pickup apparatus 1. After that, the worker performs, in the gas, the inspection whether dust is present on the entire surface of the light-receiving area of the image pickup apparatus, or whether delamination occurs on the bonding surface of the optical adhesive.

At this time, the worker disposes the first lens barrel 24 of the image pickup apparatus 1 in the exterior body insertion hole 65 of the image pickup apparatus inspection device 6A, and brings the surface of the distal end lens 21a into close contact with the first surface 7a of the angle-of-view conversion optical member 7, as shown in FIG. 6B.

With such a configuration, the pattern on the chart surface 9f, which is illuminated with the light transmitted through the transmission chart 9T, passes through the angle-of-view conversion optical member 7, to be image-formed on the light-receiving surface 31a of the image pickup device 31 of the image pickup apparatus 1.

As a result, similarly as in the above-described embodiment, the endoscopic image in which no vignetting portion exists is displayed on the display screen of the inspection apparatus, which surely enables the inspection of defect such as the inspection of whether fine dust is present or the inspection of whether delamination occurs on the bonding surface of the optical adhesive to be performed.

Note that only the housing hole main body 67m may be provided in the illumination instrument housing hole 67, without providing the light-guiding hole 67h in the illumination instrument housing hole 67, to allow the illumination lens 8a of the illumination instrument 8 to be exposed from the housing hole main body 67m.

Figure 7:
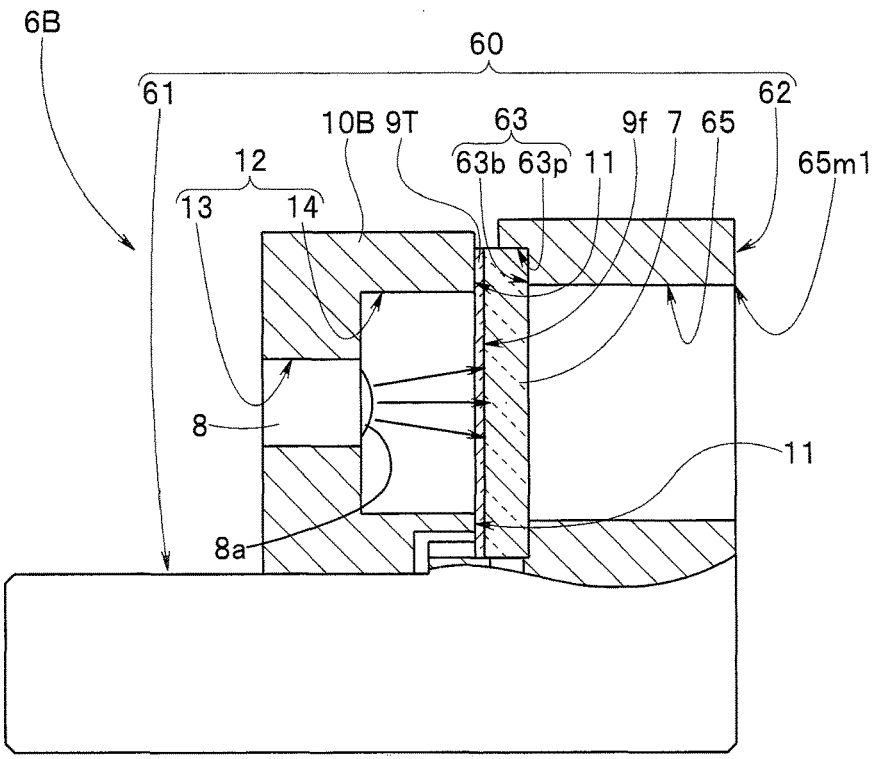
FIG. 7 illustrates another exemplary configuration of the image pickup apparatus inspection device provided with the transmission chart.

With reference to FIG. 7, another exemplary configuration of the image pickup apparatus inspection device provided with the transmission chart 9T will be described.

As shown in FIG. 7, an image pickup apparatus inspection device 6B includes a holding block 10B in the present embodiment.

The holding block 10B of the present embodiment is provided with an illumination instrument housing hole 12. The illumination instrument housing hole 12 includes a housing hole main body 13 and a light-guiding hole 14. The illumination instrument 8 is inserted in the housing hole main body 13, and housed therein in a predetermined state by a lid member, not shown, or an adhesive or the like.

In the present embodiment, the holding block 10B is integrally fixed to the support portion 61 with a bolt, not shown, to constitute the image pickup apparatus inspection device 6B, similarly as the above-described holding block 10B.

With such a configuration, the abutting surface 11 of the holding block 10B abuts the rear surface which is the opposite surface of the chart surface 9f of the transmission chart 9T, thereby capable of securely holding the angle-of-view conversion optical member 7 to which the transmission chart 9T is integrally provided.

In addition, the surface of the distal end lens 21a is disposed so as to closely contact the first surface 7a of the angle-of-view conversion optical member 7, to thereby allow the pattern on the chart surface 9f illuminated with the light transmitted through the transmission chart 9T to pass through the angle-of-view conversion optical member 7 and to be image-formed on the light-receiving surface 31a of the image pickup device 31 of the image pickup apparatus 1.

As a result, the endoscopic image in which no vignetting portion exists is displayed on the observation screen of the inspection apparatus, which enables the inspection of defect such as the inspection of whether fine dust is present or the inspection of whether delamination occurs on the bonding surface of the optical adhesive, similarly as in the above-described embodiment.

The image pickup apparatus inspection devices 6, 6A, and 6B are thus configured, which enables the inspection of the entire surface of the light-receiving area of the light-receiving surface 31a to be performed in the gas without soaking the image pickup apparatus 1 in a liquid, after the assembling of the image pickup apparatus 1 has been completed.

In addition, the inner surface of the distal end portion of the device barrel 32 is disposed at the proximal end portion of the second lens barrel 25 in the state where the first lens barrel 24 of the optical unit 2 is disposed in the exterior body insertion hole 65, and the inspection of whether dust is present on the entire surface of the light-receiving area or whether delamination occurs on the bonding surface of the optical adhesive, while performing positional adjustment such as focus adjustment.

In this case, a resolution chart and the like are formed in advance on the transmission chart by vapor deposition or sputtering, thereby enabling the inspection of the functions of the image pickup apparatus to be effectively performed, in addition to the inspection of the entire surface of the light-receiving area, during the assembling operation.

Note that the first lens barrel 24 is inserted into the exterior body insertion hole 65 to perform inspection of the image pickup apparatus 1 in the above-described embodiment. However, inspection of the endoscope may be performed by an endoscope image pickup apparatus inspection device 6C shown in FIGS. 8A and 8B.

In the description below of the endoscope inspection device 6, the same elements as those in the above-described embodiment are attached with the same reference numerals and descriptions thereof will be omitted.

Figure 8A:
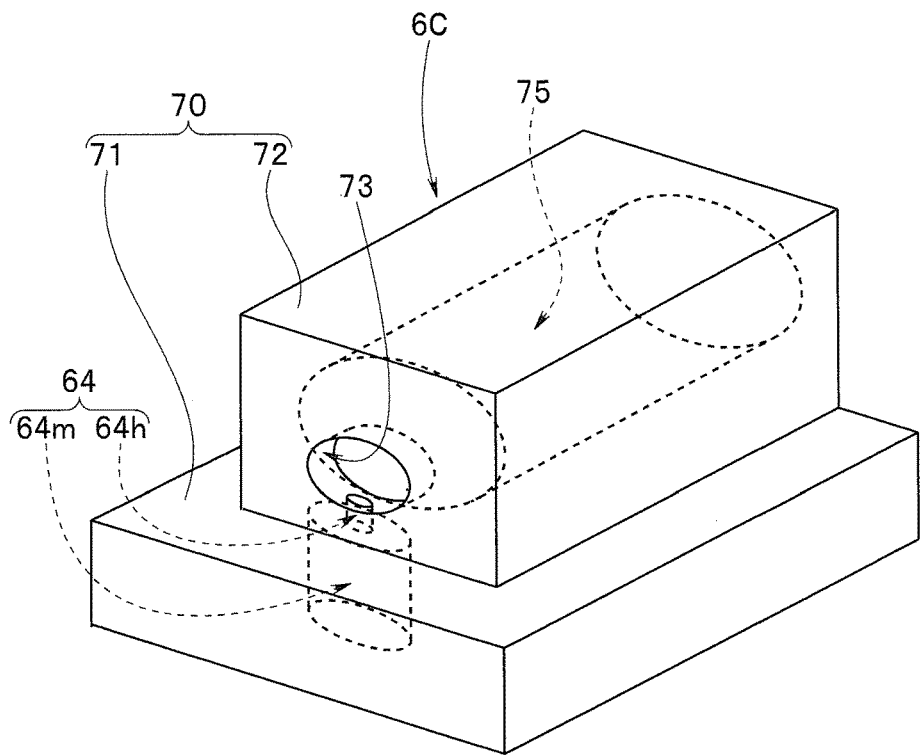
FIG. 8A illustrates a case for endoscope inspection that configures an endoscope inspection device.
Figure 8B:
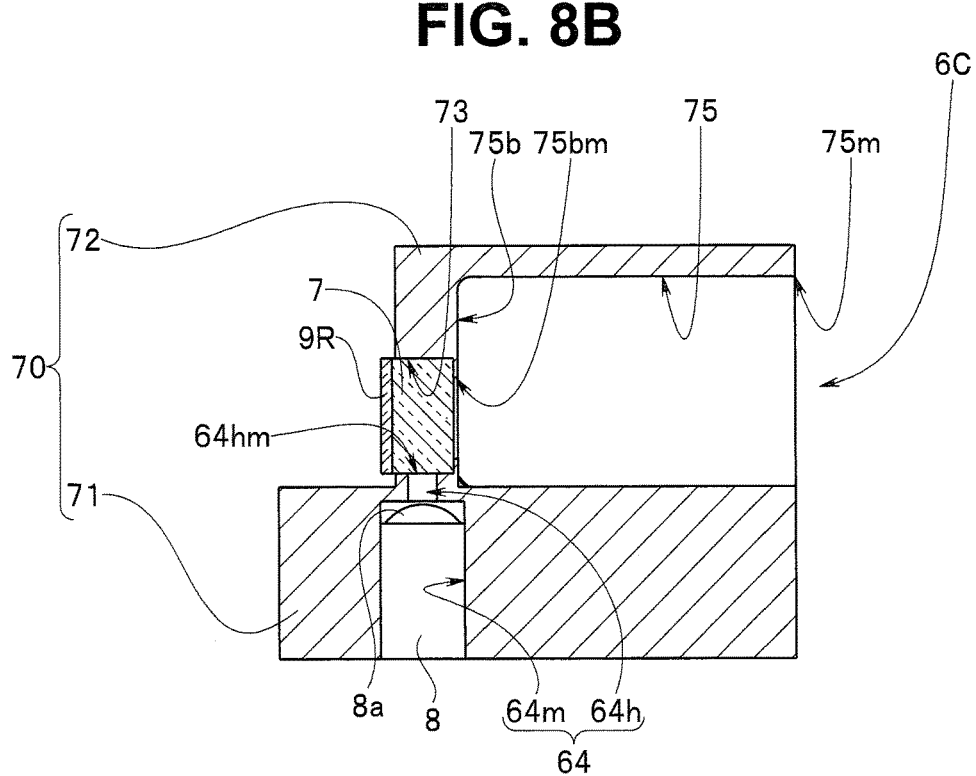
FIG. 8B illustrates the endoscope inspection device.

The endoscope image pickup apparatus inspection device 6C shown in FIGS. 8A and 8B includes a case for endoscope inspection 70 which is an inspection device main body, and the angle-of-view conversion optical member 7 to which the test chart 9 is integrally provided and the illumination instrument 8 that are arranged in the case 70.

In the present embodiment, the test chart 9 is a reflection chart 9R shown in FIG. 3.

The case for endoscope inspection 70 includes a grasping portion 71 and an endoscope inspection portion 72.

The grasping portion 71 is a part for grasping the case for endoscope inspection 70 with the hand. The endoscope inspection portion 72 is a convex portion protruded from the upper plane in the drawing, which is one surface of the grasping portion 71.

The grasping portion 71 is provided with the illumination instrument housing hole 64, and the endoscope inspection portion 72 includes an optical member housing concave portion 73 and an endoscope insertion portion housing hole 75.

The optical member housing concave portion 73 is a first attaching portion, and the inner diameter and depth of the concave portion is set in view of the outer diameter and the thickness of the angle-of-view conversion optical member 7. The angle-of-view conversion optical member 7 to which the reflection chart 9R is integrally provided is adhered and fixed to the optical member housing concave portion 73, as shown in FIG. 9B. The emission opening 64hm of the light-guiding hole 64h is formed on the inner circumferential surface 73p of the optical member housing concave portion 73.

An endoscope image pickup apparatus inspection device 6D includes, in the case for endoscope inspection 70, the angle-of-view conversion optical member 7 to which the reflection chart 9R is integrally provided and the illumination instrument 8. With such a configuration, similarly as in the above-described image pickup apparatus inspection device 6, the illumination light of the illumination instrument 8 is emitted from the emission opening 64hm, and enters the angle-of-view conversion optical member 7 from the side surface of the angle-of-view conversion optical member 7 disposed on the inner circumferential surface 73p of the optical member housing concave portion 73.

The endoscope insertion portion housing hole 75 is a third attaching portion and a straight-shaped bottomed hole, which corresponds to the outer shape of a distal end portion 82 of an endoscope 80 to be described later, for example. The endoscope insertion portion housing hole 75 includes an insertion port 75m into which the distal end portion is inserted and a bottom surface 75b to which the distal end surface of the distal end portion is disposed in proximity.

On the bottom surface 75b, a distal end lens guiding hole 75bm having a diameter smaller than the diameter of the optical member housing concave portion 73 is formed. The distal end lens guiding hole 75bm is a through hole that allows the optical member housing concave portion 73 and the endoscope insertion portion housing hole 75 to communicate with each other. The diameter of the distal end lens guiding hole 75bm is set to be larger than the outer diameter of the first lens barrel 24.

The endoscope image pickup apparatus inspection device 6C includes, in the case for endoscope inspection 70, the angle-of-view conversion optical member 7 to which the reflection chart 9R is integrally provided and the illumination instrument 8.

Figure 9A:
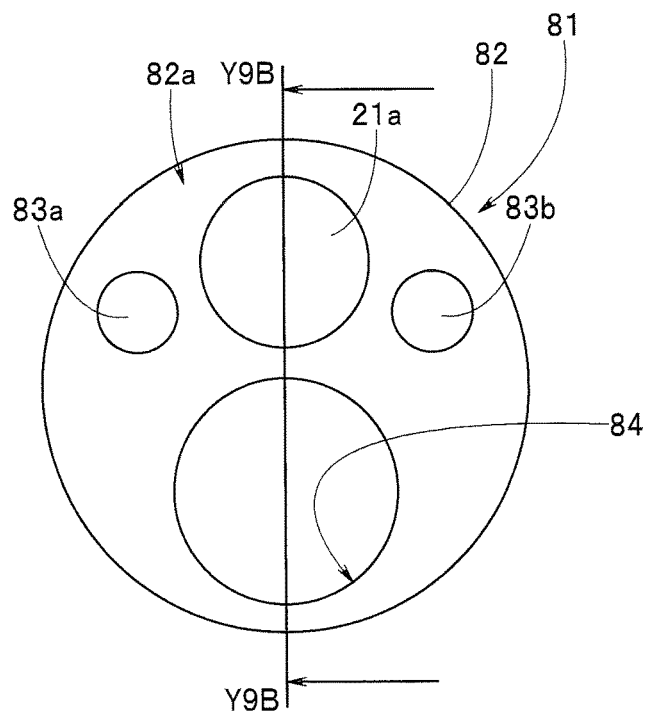
FIG. 9A illustrates a distal end surface of an insertion portion of an endoscope in which the image pickup apparatus is incorporated, which is viewed from the front.
Figure 9B:
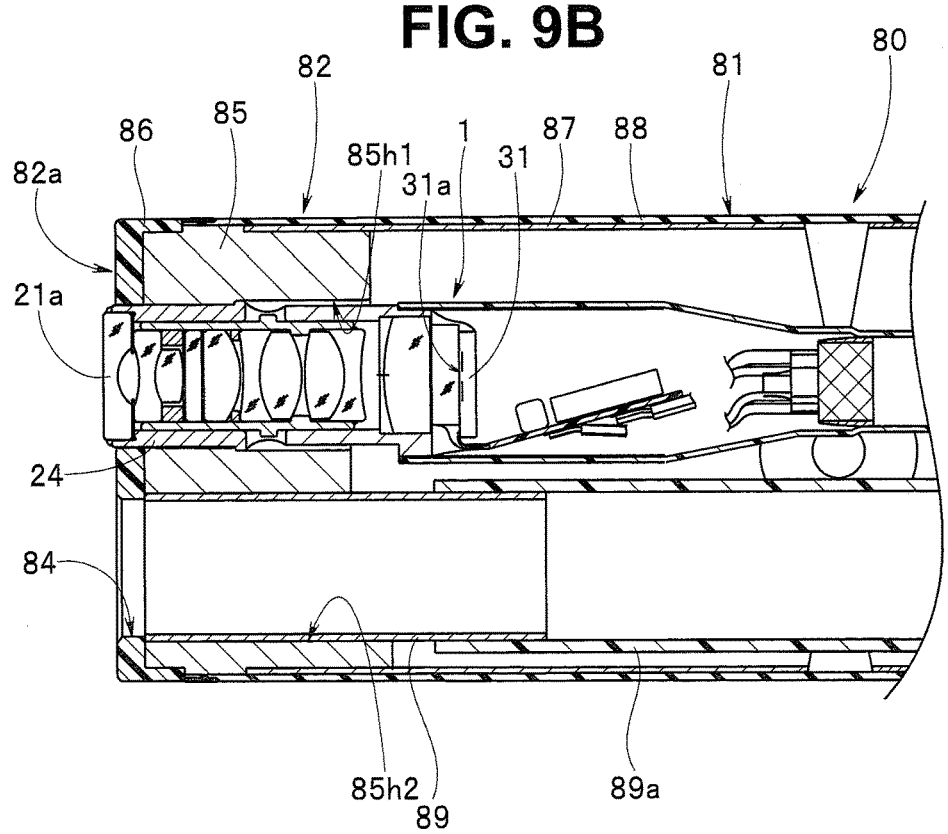
FIG. 9B is a cross-sectional view taken along the arrow line Y9B-Y9B in FIG. 9A.

In the endoscope insertion portion housing hole 75 of the endoscope image pickup apparatus inspection device 6C, the distal end side part of the insertion portion 81 of the endoscope 80 shown in FIGS. 9A, 9B is disposed.

As shown in FIG. 9A, the distal end lens 21a, the illumination lenses 83a, 83b that constitute the illumination optical system, and the opening 84 of the treatment instrument channel are provided on the distal end surface 82a of the distal end portion 82 of the insertion portion 81.

Note that FIG. 9A shows the configuration in which the two illumination lenses 83a, 83b are provided on the distal end surface 82a. However, the number of the illumination lenses is not limited to two, and may be more than two or less than two.

As shown in FIG. 9B, the image pickup apparatus 1 is disposed and fixed in an image pickup apparatus through hole 85h1 formed at a distal end rigid member 85 that constitutes the distal end portion 82 of the insertion portion 81, the distal end rigid member 85 being the exterior body of the endoscope 80. In this fixed state, the surface of the distal end lens 21a is protruded further than the distal end surface 82a.

In addition to the image pickup apparatus through hole 85h1, an illumination optical system through hole (not shown), a treatment instrument channel through hole 85h2, and the like are formed at the distal end rigid member 85. The reference numeral 86 indicates a distal end cover which is fixed to the distal end side of the distal end rigid member 85 to configure the distal end portion 82. The reference numerals 87, 88, and 89 indicate a distal end bending piece, a bending rubber, and a coupling pipe, respectively. The distal end side portion of the coupling pipe 89 is fixed in the treatment instrument channel through hole 85h2, and the distal end side portion of a channel tube 89*a* is fixed to the proximal end side portion of the coupling pipe 89.

The case for endoscope inspection 70 may be fastened and fixed to the work bench with a clamp, not shown. In addition, the illumination instrument housing hole 64 is provided at the grasping portion 71, but the illumination instrument housing hole 64 may be provided at the endoscope inspection portion 72 by appropriately deforming the shape of the endoscope inspection portion 72.

Description will be made on the working of the endoscope image pickup apparatus inspection device 6C configured as described above.

When inspection of the image pickup apparatus 1 of the endoscope 80 is performed in the gas, the worker prepares an endoscope observation apparatus including the endoscope image pickup apparatus inspection device 6C and the display screen, and turns on the illumination instrument 8, for example.

Figure 10:
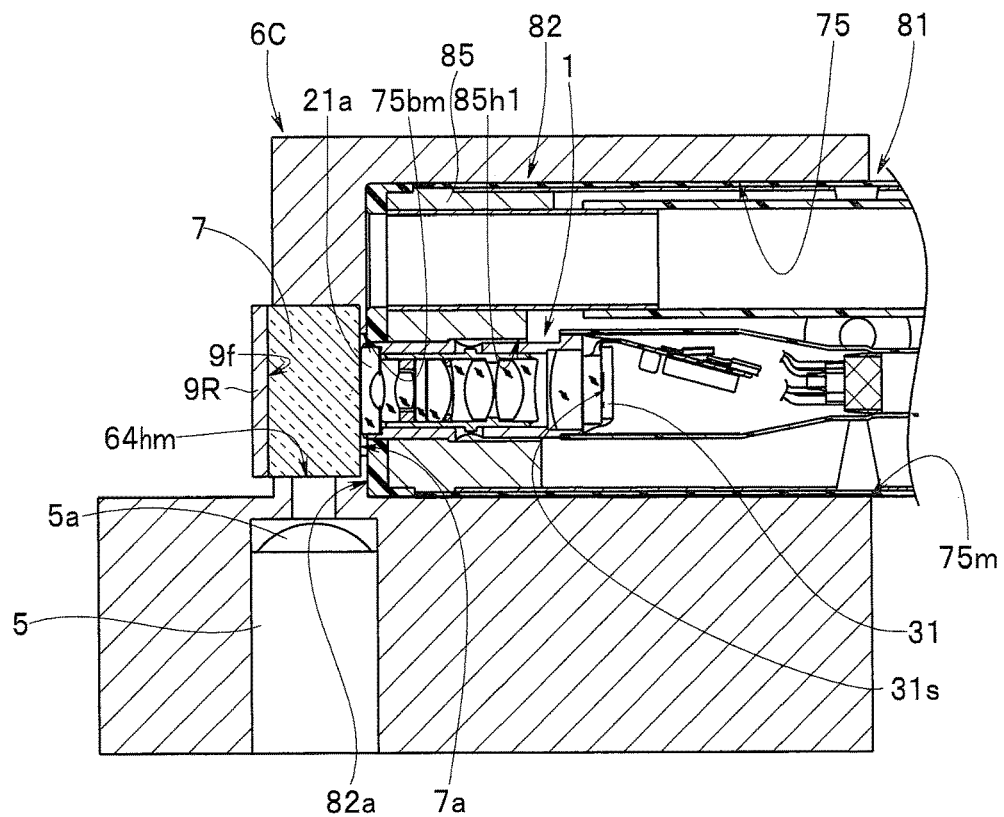
FIG. 10 illustrates an inspection state where the distal end portion of the insertion portion is disposed in the endoscope inspection device in FIG. 8B.

After that, the worker inserts the insertion portion 81 into the endoscope insertion portion housing hole 75 of the endoscope image pickup apparatus inspection device 6C, to dispose the distal end portion 82 in the endoscope insertion portion housing hole 75, as shown in FIG. 10.

Specifically, the worker grasps the insertion portion 81 to insert the distal end portion 82 from an insertion port 75*m*, and causes the distal end lens 21*a* protruded from the distal end surface 82*a* of the distal end portion 82 to advance toward the reflection chart 9R, for example. Then, the surface of the distal end lens 21*a* abuts the first surface 7*a* of the angle-of-view conversion optical member 7. At this time, the first lens barrel 24 of the image pickup apparatus 1 is disposed in the distal end lens guiding hole 75*bm*.

The worker causes the insertion portion 81 to advance in inches, to dispose the surface of the distal end lens 21*a* so as to closely contact the first surface 7*a* of the angle-of-view conversion optical member 7. As a result, the pattern on the chart surface 9*f* of the reflection chart 9R, which is illuminated with the illumination light incident on the optical member 7, passes through the angle-of-view conversion optical member 7, to be image-formed on the light-receiving surface 31*a* of the image pickup device 31 of the image pickup apparatus 1.

At this time, light is applied to the entire surface of the light-receiving surface 31*a* of the image pickup device 31 incorporated in the insertion portion 81. As a result, the endoscopic image that is formed on the entire surface of the light-receiving area of the image pickup apparatus of the cystoscope, for example, can be confirmed in the gas without soaking the cystoscope in the water.

Thus, the endoscope image pickup apparatus inspection device 6C is attached to the distal end portion of the insertion portion of the cystoscope, for example, to thereby enable an observation image same as that obtained in the in-water observation to be easily confirmed in the gas without soaking the cystoscope in the water.

Figure 11:
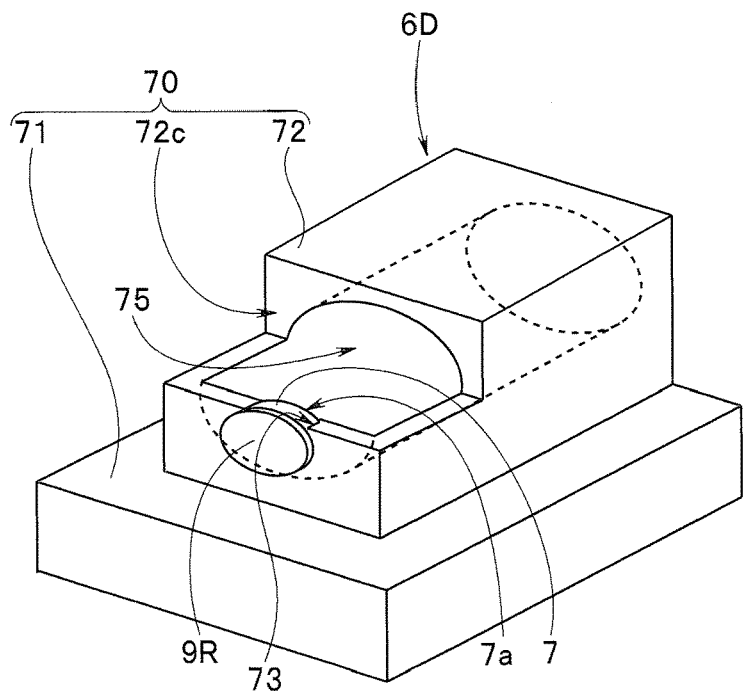
FIG. 11 illustrates an endoscope inspection device including, at an endoscope inspection portion, a cutout for allowing a distal end side part of an endoscope insertion portion housing hole to expose.

Note that an endoscope image pickup apparatus inspection device 6D may be configured such that a cutout 72*c* configured to allow the distal end side part of the endoscope insertion portion housing hole 75 to be exposed by a desired amount is formed on the optical member housing concave portion 73 side of the endoscope inspection portion 72, as shown in FIG. 11.

With such a configuration, when the insertion portion 81 of the endoscope 80 is inserted in the endoscope insertion portion housing hole 75, the distal end lens 21*a* protruded from the distal end surface 82*a* of the distal end portion 82 can be smoothly guided into the distal end lens guiding hole 75*bm*. As a result, inspection can be performed by surely causing the surface of the distal end lens 21*a* to abut the first surface 7*a* of the angle-of-view conversion optical member 7.

In addition, in the above-described embodiment, description has been made on the endoscope image pickup apparatus inspection device 6C in which the distal end portion 82 constituting the insertion portion 81 of the endoscope 80 is disposed in the endoscope insertion portion housing hole 75. However, a distal end rigid member image pickup apparatus inspection device may be configured such that a distal end rigid member housing hole may be provided instead of the endoscope insertion portion housing hole 75, to perform the inspection of whether dust is present on the entire surface of the light-receiving area of the image pickup apparatus 1 or whether delamination occurs on the bonding surface of the optical adhesive after mounting the image pickup apparatus 1 to the distal end rigid member.

Note that the present invention is not limited only to the above-described embodiment and various modifications are possible without departing from the gist of the invention.

The present invention is capable of achieving the inspection device for image pickup apparatus that is capable of performing, in the gas, the inspection of the entire surface of the light-receiving area of the image pickup apparatus used in the in-liquid endoscope without soaking the image pickup apparatus in a liquid.

What is claimed is:

1. An inspection device for image pickup apparatus comprising:
    an angle-of-view conversion optical member made of a translucent member having a predetermined refractive index, the angle-of-view conversion optical member including a first surface and a second surface that is an opposite surface of the first surface, the first surface being configured to closely contact a surface of a distal end optical member constituting an optical system of the image pickup apparatus, the surface of the distal end optical member being exposed outside of an exterior body of the image pickup apparatus, wherein a thickness from the second surface to the first surface is set to a predetermined dimension; a test chart including a chart surface provided so as to closely contact the second surface of the angle-of-view conversion optical member, an image of the chart surface being picked up by the image pickup apparatus through the angle-of-view conversion optical member; and an illumination portion that illuminates the chart surface of the test chart, wherein the test chart is a reflection chart, and the chart surface of the reflection chart is irradiated with illumination light that is emitted from the illumination portion and enters the angle-of-view conversion optical member from a side surface located between the first surface and the second surface of the angle-of-view conversion optical member.

2. An inspection device for image pickup apparatus comprising:
    an angle-of-view conversion optical member made of a translucent member having a predetermined refractive index, the angle-of-view conversion optical member including a first surface and a second surface that is an opposite surface of the first surface, the first surface being configured to closely contact a surface of a distal end optical member constituting an optical system of the image pickup apparatus, the surface of the distal end optical member being exposed outside of an exterior body of the image pickup apparatus, wherein a thickness from the second surface to the first surface is set to a predetermined dimension;

a test chart including a chart surface provided so as to closely contact the second surface of the angle-of-view conversion optical member, an image of the chart surface being picked up by the image pickup apparatus through the angle-of-view conversion optical member; and an illumination portion that illuminates the chart surface of the test chart, wherein the test chart is a transmission chart, and the chart surface of the transmission chart is irradiated with illumination light that is emitted from the illumination portion and enters the distal end optical member from a surface opposite to the chart surface of the test chart.

3. The inspection device for image pickup apparatus according to claim 1, further comprising an inspection device main body including:
    a first attaching portion to which the angle-of-view conversion optical member is attached, the angle-of-view conversion optical member being provided with the chart surface of the test chart so as to closely contact;
    a second attaching portion to which the illumination portion is attached such that the chart surface of the test chart is irradiated with the illumination light emitted from the illumination portion; and
    a third attaching portion to which the exterior body including the image pickup apparatus is attached such that the surface of the distal end optical member constituting the optical system of the image pickup apparatus closely contacts the first surface of the angle-of-view conversion optical member.

4. The inspection device for image pickup apparatus according to claim 1, wherein the translucent member is one of fluorine resin, silicone rubber, acrylic rubber, and elastomer.

* * * * *